United States Patent
Harrison et al.

(10) Patent No.: US 6,843,252 B2
(45) Date of Patent: Jan. 18, 2005

(54) SURGICAL DRAPE

(76) Inventors: Samuel W. Harrison, 4003 Scenic Dr., Shreveport, LA (US) 71119; Patrick Quick, Sr., 155 Goldsby Cir., Stonewall, LA (US) 71078; Ralph W Baucum, III, 2525 Fairfield Ave., Shreveport, LA (US) 71104

( * ) Notice: Subject to any disclaimer, the term of this patent is extended or adjusted under 35 U.S.C. 154(b) by 252 days.

(21) Appl. No.: 10/128,479

(22) Filed: Apr. 23, 2002

(65) Prior Publication Data

US 2003/0196668 A1 Oct. 23, 2003

(51) Int. Cl.[7] .................................................. A61F 5/37
(52) U.S. Cl. ..................... 128/849; 128/849; 128/853
(58) Field of Search ............................ 128/849, 853, 128/854, 852, 850, 851, 855, 856

(56) References Cited

U.S. PATENT DOCUMENTS

| | | | |
|---|---|---|---|
| 3,799,161 A | * | 3/1974 | Collins .................. 128/854 |
| 4,134,398 A | | 1/1979 | Scrivens |
| 4,316,456 A | * | 2/1982 | Stoneback ................ 128/852 |
| 4,466,430 A | | 8/1984 | Shultz |
| 4,664,103 A | | 5/1987 | Martin et al. |
| 5,322,072 A | | 6/1994 | Harrison |
| 5,546,961 A | | 8/1996 | Harrison |
| 5,611,356 A | | 3/1997 | Rothrum |
| 5,640,975 A | | 6/1997 | Diao |
| 5,901,706 A | | 5/1999 | Griesbach et al. |
| 5,988,172 A | * | 11/1999 | Sosebee ................ 128/849 |
| 6,055,987 A | | 5/2000 | Griesbach et al. |
| 6,216,700 B1 | | 4/2001 | Griesbach et al. |
| 6,298,855 B1 | | 10/2001 | Baird |
| 6,314,959 B1 | | 11/2001 | Griesbach et al. |

* cited by examiner

Primary Examiner—Henry Bennett
Assistant Examiner—Camtu Nguyen
(74) Attorney, Agent, or Firm—Mark J. Young

(57) ABSTRACT

A surgical drape for use in connection with a sterility maintenance cover has an opening that corresponds to an open window in a sterility maintenance cover to facilitate ventilation and access to a patient's head, a window that corresponds to a window in a sterility maintenance cover to enhance patient comfort and observation, and attachment means for releasably attaching the drape to a sterility maintenance cover, and one or more fenestrations to facilitate surgical access at desired locations.

22 Claims, 5 Drawing Sheets

SURGICAL DRAPE

BACKGROUND OF THE INVENTION

1. Field of the Invention

The present invention relates generally to surgical drapes. More particularly, the present invention relates to a surgical drape for use with a sterility maintenance cover.

2. Background Description

During certain surgical procedures, such as pacemaker implants and similar procedures, it is imperative that a patient's head be draped in a sterile manner to insure that a sterile field is maintained throughout the operation. Various methods have been employed to achieve this result, including various types of draping techniques, using supports and other devices. For example, U.S. Pat. No. 5,322,072 to Harrison et al. and U.S. Pat. No. 5,546,961 to Harrison (the "Harrison patents") teach sterility maintenance covers that support a surgical drape over a patient's head. Such a sterility maintenance cover generally includes (i) a base panel for fitting under the head, neck and shoulders of a patient positioned on an examination or operating table, (ii) an upward-standing end panel extending from the base panel and having an open window for accessing the patient from the end or side of the table, and (iii) a cantilevered platform projecting horizontally from the end panel, substantially parallel to the base panel, over the patient's head and neck. In a preferred embodiment, the platform is designed to support a drape over a patient's head and/or to receive and retain or deploy various instruments used in the procedure. Also in a preferred embodiment, the sterility maintenance cover includes one or more windows to facilitate access to and observation of the patient's head.

As used herein, "sterility maintenance cover" refers to any structure that supports a surgical drape over a patient's head, preventing the drape from lying directly on the patient's face. Such sterility maintenance covers include sterility maintenance covers as described in the Harrison patents, as well as other similar devices such as three-dimensional frames.

Improper draping can cause serious problems and defeat the effectiveness of the sterility maintenance cover. For example, a conventional surgical drape applied insecurely over a sterility maintenance cover creates a substantial risk that the drape or a portion of it will move, exposing all or part of the patient's head during surgery. Various forces applied directly or indirectly to the drape by surgeons, assistants, instrumentation and the like may cause such movement. The exposure can contaminate a sterile field, increasing risk of infection, and expose the patient's head to blood and other bodily fluids.

Similarly, applying conventional flat sheet surgical drapes over a three-dimensional sterility maintenance cover may create unintended gaps, exposing all or part of the patient's head during surgery. Again, the exposure can contaminate a sterile field, increasing risk of infection, and expose the patient's head to blood and other bodily fluids.

Additionally, conventional surgical drapes, which do not include transparent windows or openings that correspond to windows or openings in a sterility maintenance cover, tend to visually conceal the patient's head in its entirety or substantial part. From the surgeon's perspective, such visual concealment may prevent observation of potential surgical problems and complications. For example, a nasal cannula or mask may come lose during surgery thereby preventing a patient from properly receiving supplemental oxygen and possibly trapping dangerous concentrations of oxygen under the drape. Even worse, a patient may vomit during surgery (e.g., if there is food in an anesthetized patient's stomach) with the stomach contents entering the windpipe and lungs, possibly causing pneumonia or even death. From the patient's perspective, particularly a patient who is awake at the start or throughout their surgery, such visual concealment deprives the patient of the opportunity to talk with the circulating nurse and may create a sense of claustrophobia, while contributing to anxiety and panic. Such emotional responses can adversely affect blood pressure and heart rate, which may also complicate a procedure.

Furthermore, conventional surgical drapes, which do not include openings that correspond to openings in a sterility maintenance cover, may cause unwanted increases in temperature and buildup of gasses. For example, a patient's exhalation under such a drape can make a patient feel warm, sweaty and uncomfortable. Concomitantly, levels of trapped carbon dioxide ($CO_2$) (a prominent component of exhaled air) and/or supplemental oxygen may rise under the drape, creating substantial risks of hypercarbia and surgical fire, which may be sparked by electrosurgical units, lasers, certain drills, fiber optic devices, and electrocautery units.

Moreover, many conventional surgical drapes that include openings or apertures (more commonly known in the medical field as "fenestrations") to facilitate surgical procedures have very limited utility when used in connection with a sterility maintenance cover. The fenestrations are typically located on the drape proximate to regions requiring surgical access. As such drapes typically do not include enough head-end material to drape over a sterility maintenance cover without causing the fenestrations to move away from the intended region, multiple drapes must be used. One drape may be used for the sterility maintenance cover, and another drape for the patient. Such draping, however, is inefficient and conducive to many of the draping problems discussed above.

Manually cutting a conventional drape with scissors or a knife to provide an opening creates similar problems. First, such manual operations consume valuable time and tend to be imprecise, often leading to improperly sized and placed openings. Oversized openings may compromise a sterile field and over-expose the patient's head to blood and fluids. Undersized and improperly placed openings visually conceal the patient's head, limit accessibility and risk trapping gases. Furthermore, such cutting may create rough, tattered or frayed edges that are conducive to lint generation. Fine pieces of lint may be inhaled by the patient, contaminate a sterile field and even enter the surgical site.

In sum, existing surgical drapes are not well suited for use with sterility maintenance covers, as they do not include attachment means for securing them to the sterility maintenance covers, lack sufficient head-end drape material to cover a sterility maintenance cover and omit features (e.g., cutouts and transparent windows) corresponding to openings and/or windows in the sterility maintenance covers. Consequently, use of conventional surgical drapes with a sterility maintenance cover, may give rise to the aforementioned serious risks. Thus, there is a need for a surgical drape that specifically accommodates sterility maintenance covers.

SUMMARY OF THE INVENTION

The present invention provides a suitably sized surgical drape with an opening that corresponds to an open window in a sterility maintenance cover, a window that corresponds to a window in a sterility maintenance cover, and attachment means for releasably attaching the drape to a sterility maintenance cover.

It is therefore an object of the present invention to provide a surgical drape useable with existing sterility maintenance covers that facilitates access to a patient's head without compromising sterility.

It is also an object of the present invention to provide a surgical drape having an opening that corresponds to an opening in a sterility maintenance cover to facilitate access to a patient's head.

It is another object of the present invention to provide a surgical drape having a transparent window that corresponds to a window or opening of a sterility maintenance cover to provide visibility.

It is yet another object of the present invention to provide a surgical drape having a releasable attachment means to securely fasten the drape to a sterility maintenance cover.

It is a further object of the present invention to provide a surgical drape that is suitably sized for use in connection with a sterility maintenance cover wherein the drape has at least one fenestration located to facilitate a desired surgical procedure.

It is yet a further object of the present invention to provide a surgical drape having a form-fitted hood for placement over a sterility maintenance cover.

Further advantages of the present invention will be apparent from the description below with reference to the accompanying drawings, wherein like numbers refer to like elements in the several drawings.

DETAILED DESCRIPTION OF A PREFERRED EMBODIMENT OF THE INVENTION

Figure 1:
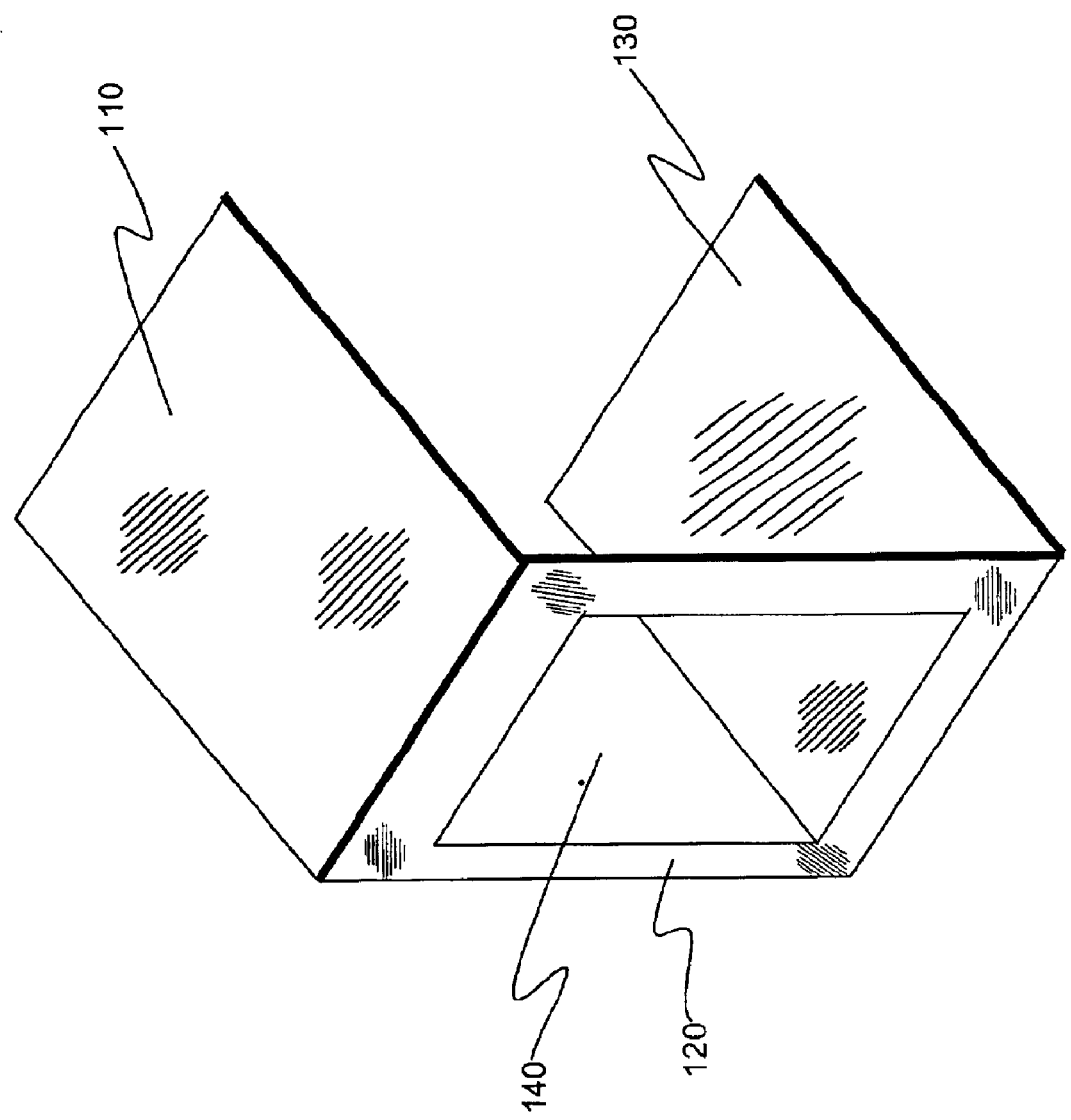
FIG. 1 conceptually illustrates an exemplary sterility maintenance cover for use in connection with a surgical drape according to the present invention.

Referring now to FIG. 1, an exemplary sterility maintenance cover for use in connection with a surgical drape according to the present invention is conceptually shown. The sterility maintenance cover generally includes (i) a base panel 130 for fitting under the head, neck and shoulders of a patient positioned on an examination or operating table, (ii) an upward-standing end panel 120 extending from the base panel and having an open window 140 for accessing the patient from the head-end of the table, and (iii) a cantilevered platform 110 projecting horizontally from the end panel, substantially parallel to the base panel. Preferably, platform 110 is designed to support a drape over a patient's head and to receive and retain or deploy various instruments used in the procedure.

Figure 2:
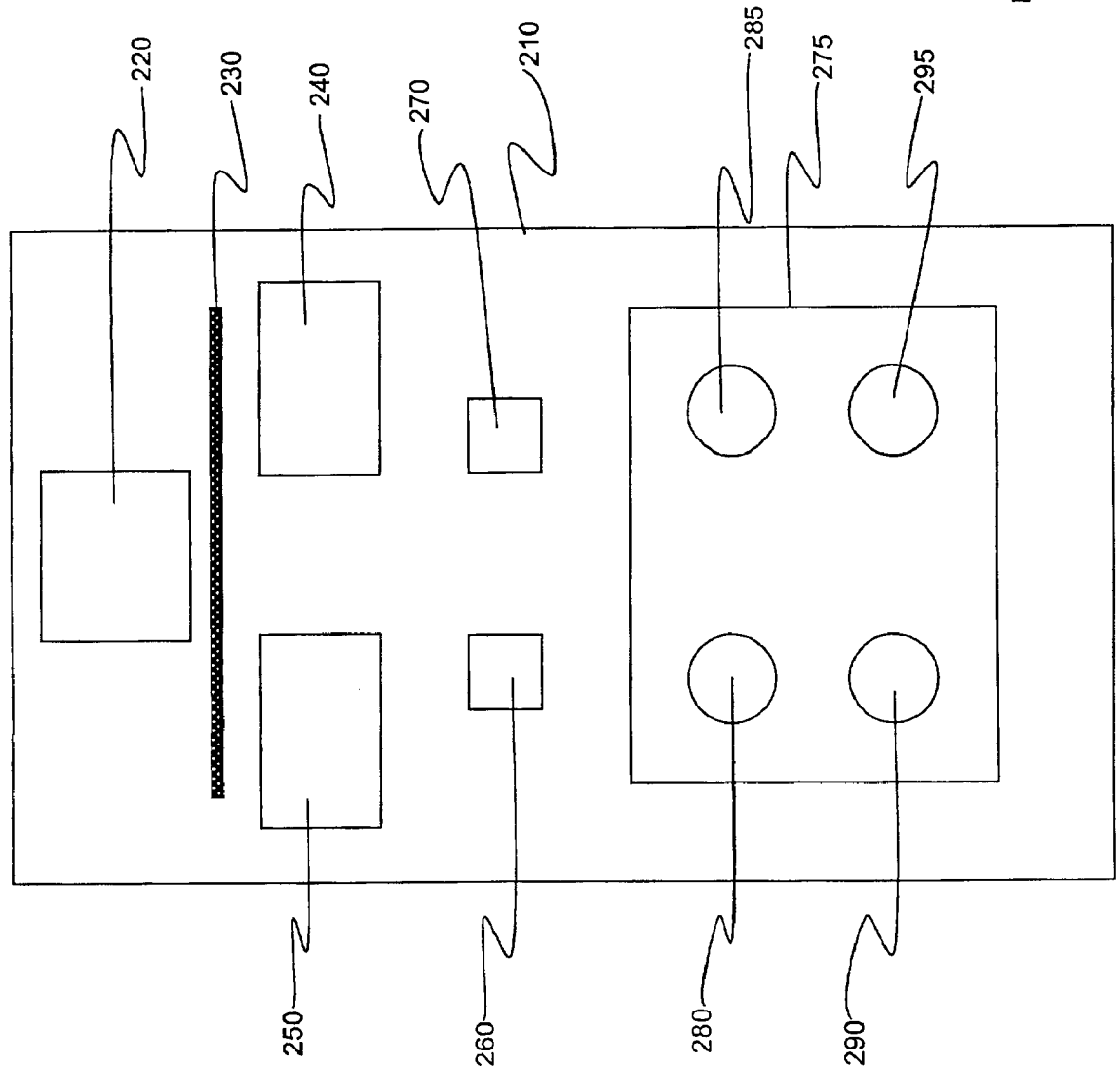
FIG. 2 is a conceptual plan view of an exemplary surgical drape according to the present invention.

Now referring to FIG. 2, a top plan view of an exemplary surgical drape 210 in accordance with a preferred embodiment of the present invention is shown. The drape 210 preferably includes an open window 220; transparent windows 240 and 250; releasable attaching means 230; a plurality of fenestrations 260, 270 and 280–295; and an absorbent liner 275.

When the surgical drape 210 is draped over a sterility maintenance cover, open window 220 (i.e., a patient access panel or access cutout) preferably aligns substantially with open window 120 of the sterility maintenance cover. Transparent windows 240 and 250 (i.e., side panels for viewing or accessing the head of the patient) preferably align substantially with the open sides of the sterility maintenance cover. Releasable attaching means 230 preferably aligns substantially with a determined portion of the sterility maintenance cover for releasable attachment.

The open window 220 enhances patient comfort while facilitating observation, ventilation and access, such as for supplemental oxygen administration. The open window 220 may be comprised of a cutout from the surgical drape 210 or a perforated portion that may be removed as desired. The cutout may be uncovered or may be covered with a removable patch. In the latter case, the patch may be removed to expose the open window as desired.

The drape 210 preferably is sufficiently sized to cover a sterility maintenance cover, a patient from head-to-toe, and a surgical table. The length and width may depend upon various factors, including the dimensions of the sterility maintenance cover, the dimensions of the surgical table and the size of the patient. A length measuring approximately one hundred inches, and a width measuring approximately seventy-two inches should suffice for most applications. While some excess drape material is not problematic in most cases, it would be unnecessary and undesirable for the drape's edges to reach the floor, present a slipping hazard, or conceal control mechanisms for the surgical table or equipment.

The drape 210, including fenestrations 260, 270 and 280–295 and absorbent liner 275, may be comprised of any of a variety of materials known in the surgical drape art. For example, a drape according to the present invention may include a nonwoven surface layer of spunbond fabric joined to an impermeable barrier layer by a meltblown adhesive layer. The materials should be flexible and provide a protective barrier that has low lint generation characteristics, is flame retardant, is resistant to strikethrough. Some examples of suitable materials known in the art are disclosed in U.S. Pat. Nos. 4,041,203; 6,298,855; and 6,314,159.

Transparent windows 240 and 250 enhance patient comfort while facilitating observation. They may be comprised of any of a variety of flexible transparent materials known in the art. Alternatively, one or both of transparent windows 240 and 250 may be comprised of an opening, which would not provide a protective barrier but would improve ventilation and access, such as for supplemental oxygen administration. The opening may be comprised of a cutout from the surgical drape 210 or a perforated portion that may be removed as desired. The cutout may be uncovered or may be covered with a removable patch. In the latter case, the patch may be removed to expose the open window as desired.

The fenestrations 260, 270 and 280–295 facilitate surgical access. They may be comprised of any of a variety of materials known in the surgical drape art. For example, an adhesive material may be attached to the periphery of the drape material about the fenestration so that the drape can be held in place around the surgical site and so that blood will not pass between the drape and the patient's body. The combination of the drape itself and the adhesive material around the perimeter of the fenestration ensures a barrier between the surgical wound and the remainder of the body. Some drapes may utilize incise materials which extend over the fenestration. Such incise materials are typically transparent plastic films having an adhesive side which adheres to the surgical site of the patient. Such drapes may be secured to the patient by at least the incise material.

The number, location, size, and shape of the fenestrations 260, 270 and 280–295 may depend upon the surgical procedures for which the drape is designed. Generally, each fenestration should be at least large enough to provide for an opening of a size to accommodate a desired incision. The fenestrations 260, 270 and 280–295 should be located proximate to regions of the patient's body where surgical access is desired, taking into account use of the drape 210 with a sterility maintenance cover. For example, fenestrations conceptually shown in FIG. 2 are located at predetermined positions for anterior pectoral, deltoid pectoral and antegrade femoral access, allowing for subclavian access as well as femoral percutaneous access. Including such multiple fenestrations on a drape allows for multiple predetermined surgical access sites for invasive procedures without having to replace or relocate the drape for each surgical access, thus ensuring a consistent surgical field.

The absorbent liner 275 located around the bilateral femoral access fenestrations 280 and 285 and at the superior of the drape facilitates the containment of bodily fluids encountered during a procedure. The absorbent liner 275 may be formed from a variety of materials, including a multi-layer laminate which includes a fluid-absorbing material that may be backed by a fluid-repellant or fluid-impervious film layer. A variety of attachment mechanisms may be used to secure the liner 275 to the upper surface of the drape, such as, for example, adhesive, stitching, thermal or ultrasonic bonding.

An absorbent liner may be provided for an individual fenestration, surrounding the fenestration to absorb fluids emitted therefrom. Each fenestration may have its own absorbent liner. Alternatively, as shown, multiple fenestrations 280–295 may share a single absorbent liner 275.

The releasable attaching means 230 is located on the underside of the drape and offers the drape a secure, positive placement. The releasable attaching means 230 may be comprised of any of a variety of releasable attaching means known in the art, including tape, adhesive strips, hook-and-loop Velcro®-type fasteners or other mechanical fasteners for releasably attaching the drape to a sterility maintenance cover. For example, the releasable attaching means 230 may be comprised of an adhesive strip. Hook-and-loop Velcro®-type fasteners and other mechanical fasteners may require affixing a fastener component to the drape and a cooperating fastener component to the sterility maintenance cover.

Directions may be stamped, printed or adhered to the drape to indicate how the drape is to be placed on the patient and used in conjunction with a sterility maintenance cover. For example, explanatory text, arrows and diagrams, may be utilized and applied to the surgical drape in any of a wide variety of manners.

Figure 3:
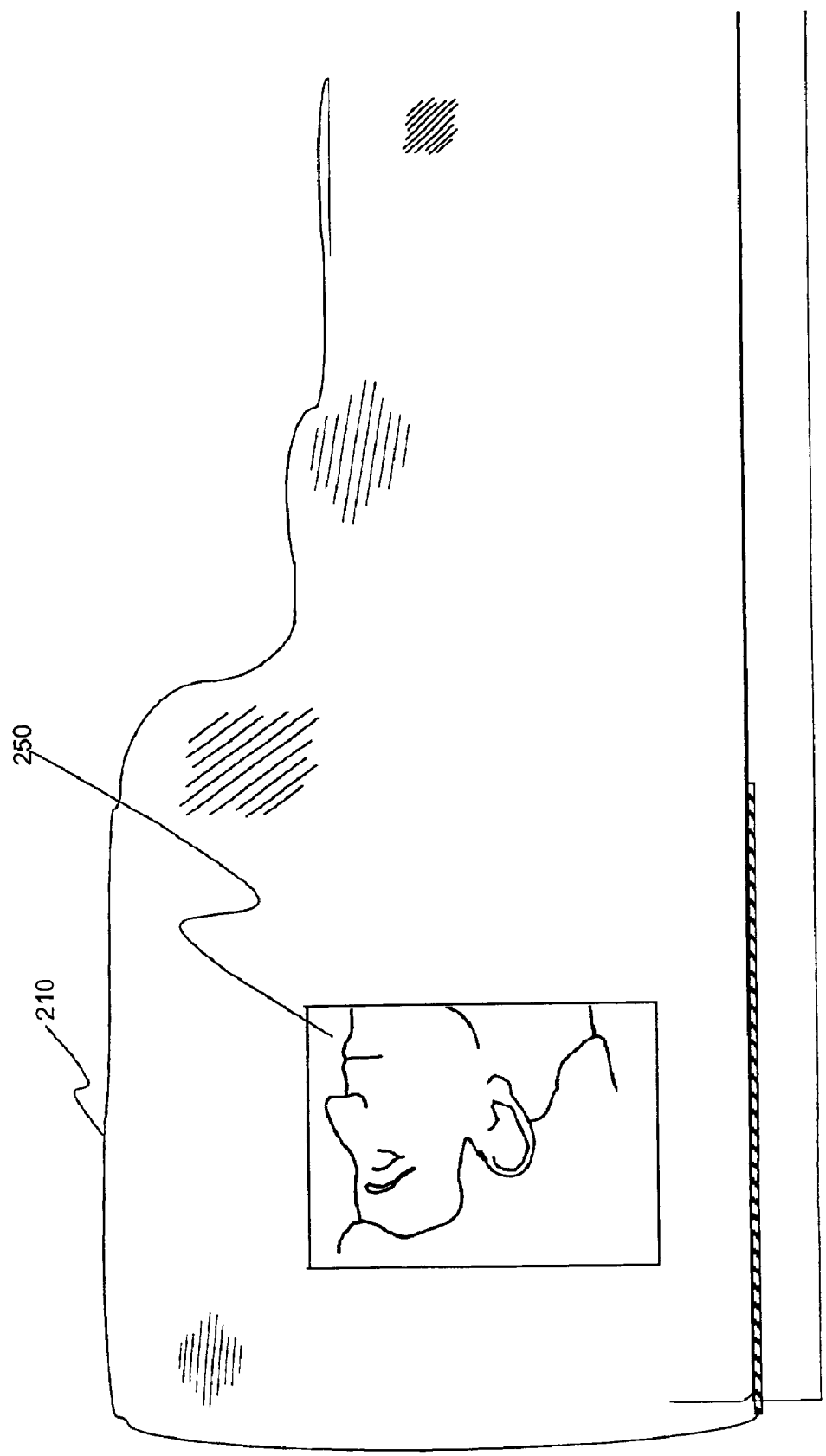
FIG. 3 conceptually illustrates an exemplary surgical drape according to the present invention in use with a sterility maintenance cover, which is covered by the surgical drape.

Turning to FIG. 3, the drape 210 of FIG. 2, is conceptually shown draped in place over a sterility maintenance cover and a patient. The window 250, which may be comprised of a transparent material or an opening, facilitates observation of the patient, while enhancing the patient's comfort.

Figure 4:
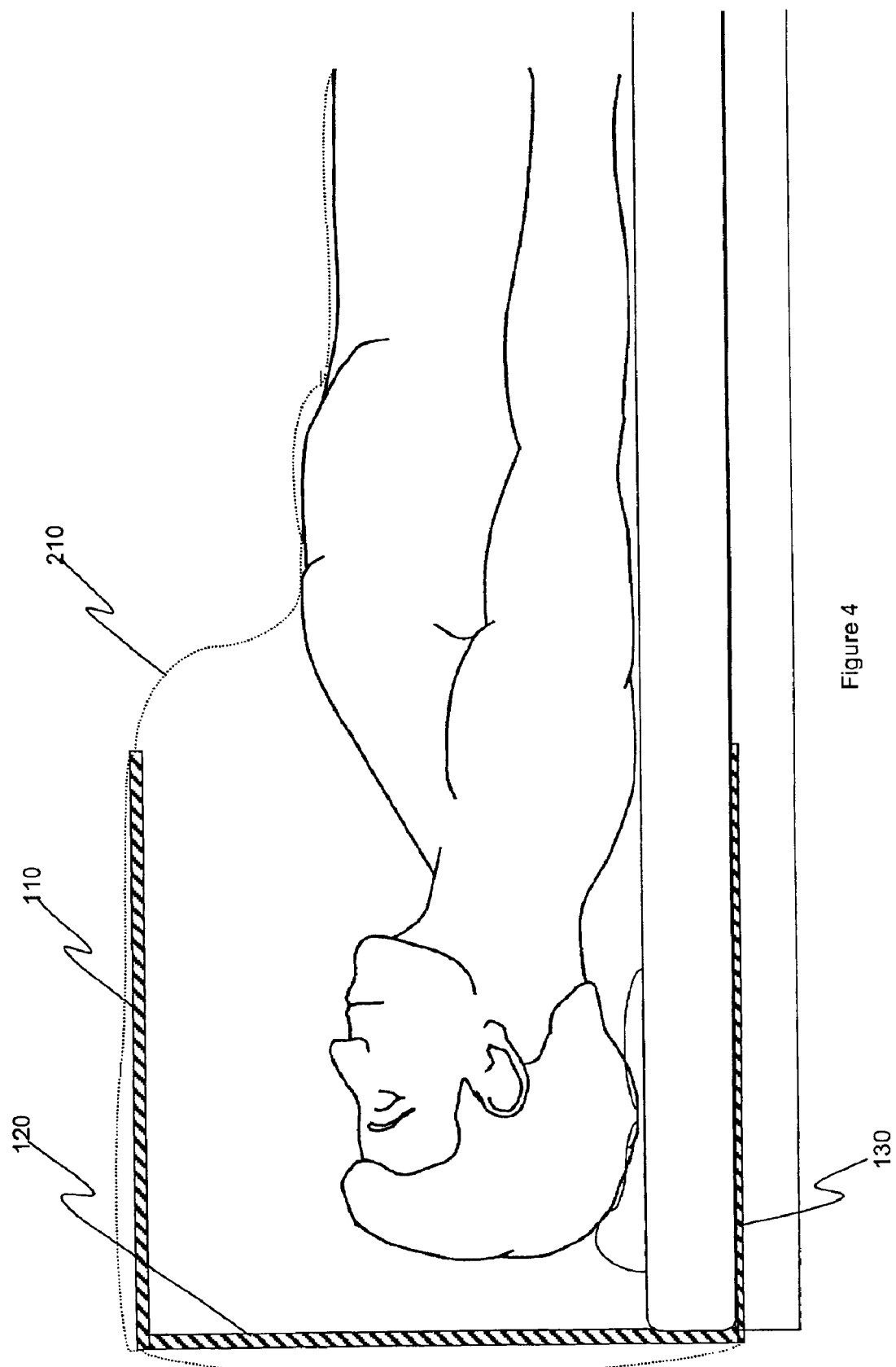
FIG. 4 conceptually illustrates a cross-sectional view of an exemplary surgical drape according to the present invention in use with a sterility maintenance cover.

Similarly, FIG. 4 conceptually shows a cross sectional view of the drape 210 (denoted with dotted lines) in place over the sterility maintenance cover and patient.

Figure 5:
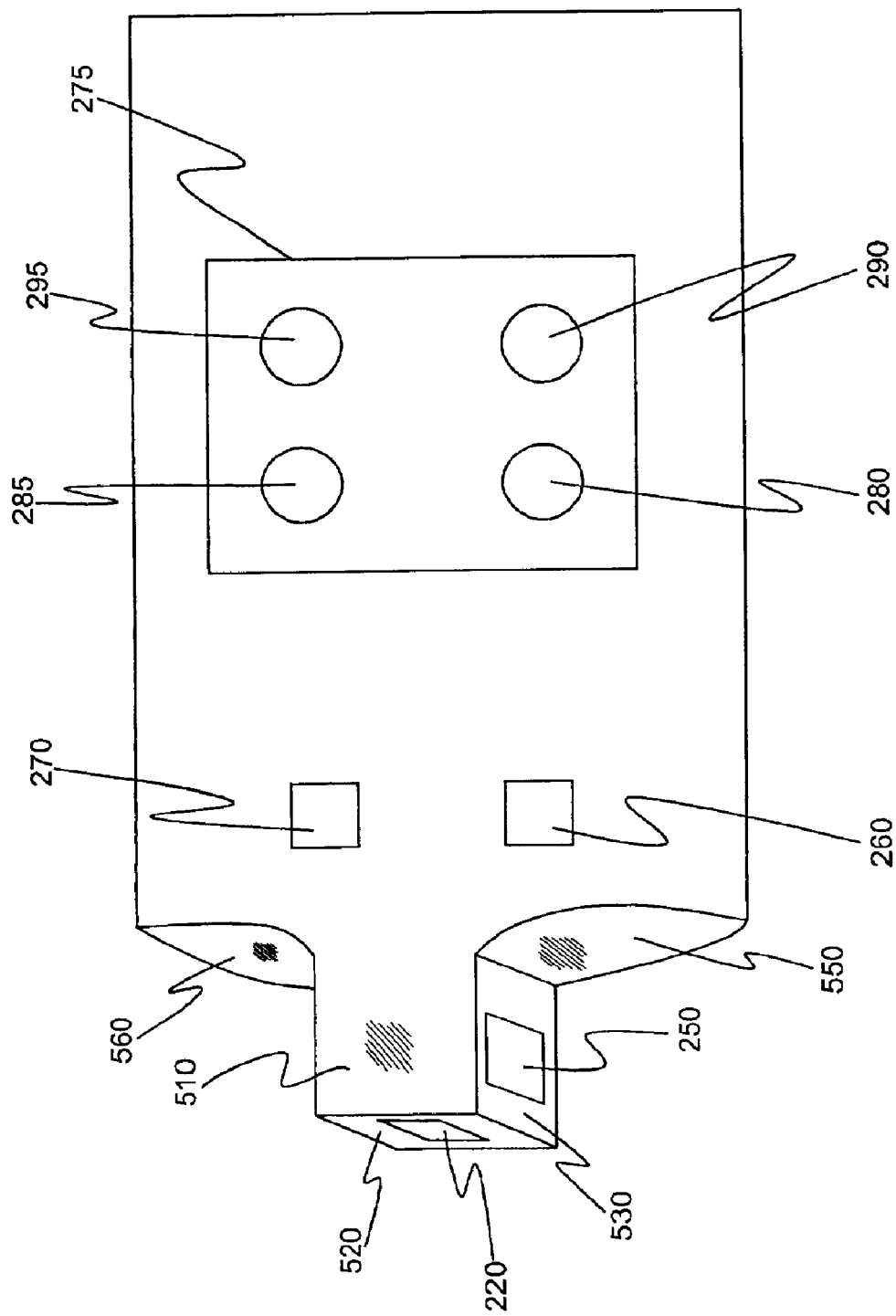
FIG. 5 conceptually illustrates an exemplary surgical drape according to the present invention having a form-fitted hood for placement over a sterility maintenance cover of the type depicted in FIG. 1.

In an alternative preferred embodiment, a drape in accordance with the present invention may include a form-fitted hood designed to "custom fit" over the sterility maintenance cover, as conceptually shown in FIG. 5. The form-fitted hood comprised of a plurality of panels at the head-end of the drape, preferably including a top panel 510 for covering the platform 110 of the sterility maintenance cover, a panel 520 with an open window 220 for substantial alignment with the upward-standing end panel 120 and open window 140 of the sterility maintenance cover, and opposing side panels 530 and 540 (540 not shown) with transparent windows 240 and 250 (240 not shown) to facilitate observation. Though the form-fitted hood may have various shapes and dimensions, it is preferably shaped and sized to neatly fit over the sterility maintenance cover. Shoulder panels 550 and 560 may also be provided for covering the shoulders of the patient.

The form-fitted hood facilitates proper positioning and secure placement, prevents slipping and eliminates excess material. It may be used in addition to or in lieu of a releasable attaching means 230. Those skilled in the art will appreciate that the form-fitted hood may be tailored to accommodate a variety of sterility maintenance cover configurations without departing from the scope of the present invention.

While the invention has been described in terms of its preferred embodiments, those skilled in the art will recognize that the invention can be practiced with modifications within the spirit and scope of the appended claims. For example, a sterility maintenance cover may have a different construction than the sterility maintenance cover conceptually shown in FIG. 1, with more or fewer open windows and with open, closed or partially closed sides. In which case, a surgical drape in accordance with the present invention may include such corresponding open windows, transparent windows and modifications to work with the sterility maintenance cover and provide access and visibility to the patient's head. Such alternative surgical drapes are intended to come within the scope of the present invention.

Additionally, a drape in accordance with the present invention may include various additional features and elements known in the surgical drape art, such as pouches, tabs for attaching hoses and equipment, additional adhesive strips, and perforations and scores for controlled tearing of the drape. Such surgical drapes are also intended to come within the scope of the present invention.

It is intended that the present invention include such modifications and variations as come within the spirit and scope of the appended claims and their equivalents. Thus, it is intended that all matter contained in the foregoing description or shown in the accompanying drawings shall be interpreted as illustrative rather than limiting, and the invention should be defined in accordance with the following claims and their equivalents.

What is claimed is:

1. A surgical drape for providing a sterile field about a patient during a surgical procedure performed using a sterility maintenance cover, said surgical drape comprising:
   a pre-sterilized sheet of material, said sheet of material comprising:
   an open window configured for substantial alignment with an observation window of the sterility maintenance cover;

a transparent window configured for substantial alignment with an open side of the sterility maintenance cover while said open window is substantially aligned with the observation window:

at least one fenestration, said at least one fenestration located in a vicinity of at least one surgical site; and means for securing said pre-sterilized sheet to the sterility maintenance cover.

2. The surgical drape according to claim 1, wherein said at least one fenestration further comprises an adhesive border for securing said surgical drape to the patient.

3. The surgical drape according to claim 1, wherein said at least one fenestration further comprises at least one pectoral access fenestration.

4. The surgical drape according to claim 3, wherein said at least one pectoral access fenestration further comprises an anterior pectoral access fenestration and a deltoid pectoral access fenestration.

5. The surgical drape according to claim 1, wherein said at least one fenestration further comprises at least one femoral access fenestration.

6. The surgical drape according to claim 5, further comprising an absorptive lining surrounding said at least one femoral access fenestration.

7. The surgical drape according to claim 1, further comprising at least one side panel for viewing or accessing a head of the patient.

8. The surgical drape according to claim 7, wherein said at least one side panel comprises at least one transparent window for viewing the head of the patient.

9. The surgical drape according to claim 7, wherein said at least one side panel comprises at least one cutout for accessing the head of the patient.

10. The surgical drape according to claim 7, wherein said at least one side panel comprises at least one perforated panel for accessing the head of the patient.

11. The surgical drape according to claim 1, wherein said means for securing comprises a hook-and-loop fastener.

12. The surgical drape according to claim 1, wherein said means for securing comprises an adhesive strip.

13. The surgical drape according to claim 1, wherein said means for securing comprises a form-fitted hood.

14. A surgical drape for providing a sterile field about a patient during a surgical procedure using a sterility maintenance cover, said surgical drape comprising:

a sterilized sheet, said sterilized sheet comprising:

at least one patient-access panel, said patient access panel including a first window configured for substantial alignment with an observation window of the sterility maintenance cover;

a second window configured for substantial alignment with an open side of the sterility maintenance cover, while said first window is substantially aligned with the observation window;

at least one fenestration; and an absorptive material surrounding said at least one fenestration.

15. The surgical drape according to claim 14, wherein said at least one fenestration further comprises an adhesive border.

16. The surgical drape according to claim 14, further comprising a hook and loop fastener for securing said surgical drape to a sterility maintenance cover.

17. The surgical drape according to claim 14, further comprising an adhesive strip for securing said surgical drape to a sterility maintenance cover.

18. The surgical drape according to claim 14, further comprising a form-fitted cover for securing said surgical drape to a sterility maintenance cover.

19. A surgical drape for providing a sterile field about a patient during a surgical procedure using a sterility maintenance cover said surgical drape comprising:

a unitary sheet of material, said sheet of material comprising:

a head covering portion, said head covering portion including at least one head access cutout configured for substantial alignment with an observation window of a sterility maintenance cover and a window configured for substantial alignment with an open side of the sterility maintenance cover while said head access cutout is substantially aligned with the observation window; and a body covering portion, said body covering portion including at least one fenestration, said one fenestration being configured for alignment with a determined surgical site.

20. The surgical drape according to claim 19, wherein said at least one head access cutout is a located for substantial alignment with an observation or access port of a sterility maintenance cover.

21. The surgical drape according to claim 20, further comprising means for securing said surgical drape to the sterility maintenance cover.

22. The surgical drape according to claim 19, wherein said body covering portion further comprises an absorptive liner for absorbing bodily fluids.

* * * * *